(12) United States Patent
Skaggs

(10) Patent No.: US 7,915,209 B1
(45) Date of Patent: Mar. 29, 2011

(54) INDIVIDUAL LIQUID-FILLED SOAP BAR

(76) Inventor: Linda Skaggs, Pinellas Park, FL (US)

( * ) Notice: Subject to any disclaimer, the term of this patent is extended or adjusted under 35 U.S.C. 154(b) by 937 days.

(21) Appl. No.: 11/686,711

(22) Filed: Mar. 15, 2007

(51) Int. Cl.
*A61K 7/50* (2006.01)

(52) U.S. Cl. .......................... 510/141; 510/146; 510/152

(58) Field of Classification Search .................. 510/141, 510/146–147, 144
See application file for complete search history.

(56) References Cited

U.S. PATENT DOCUMENTS

| | | |
|---|---|---|
| 1,993,174 A | 3/1935 | Le Coney |
| 2,470,851 A | 5/1949 | Hermanson |
| 2,539,395 A | 1/1951 | Banks |
| 2,636,008 A | 4/1953 | Jurgensen et al. |
| 3,186,869 A | 6/1965 | Friedman |
| 4,718,556 A | 1/1988 | Hildebrandt |
| 6,187,728 B1 * | 2/2001 | McManus ...................... 510/142 |
| 6,720,296 B1 * | 4/2004 | Bitton ........................... 510/141 |

* cited by examiner

*Primary Examiner* — Necholus Ogden, Jr.
(74) *Attorney, Agent, or Firm* — Larson & Larson, P.A.; Frank Liebenow; Justin Miller

(57) ABSTRACT

An application for an individual liquid-filled soap includes a thin, breakable, solid soap outer shell and a liquid contained within the thin, solid soap outer shell. The liquid is either liquid soap or a soap-compatible liquid such as lanolin, hand cream, antibacterial soap, and antibacterial cream or a combination of these ingredients.

18 Claims, 3 Drawing Sheets

INDIVIDUAL LIQUID-FILLED SOAP BAR

FIELD OF THE INVENTION

This invention relates to the field of soap and more particularly to a liquid-filled individual serving of bar soap.

BACKGROUND OF THE INVENTION

Often, one winds up in a friend's or relative's bathroom, wanting to wash their hands, only to find a typical bar of soap impregnated with dirt, grease and assorted hair. Alternately, one might find a liquid soap dispenser, the top of which is also covered with dirt and grease. Using the liquid soap dispenser often results in a trail of liquid soap from the dispenser to the sink basin.

To combat this problem, soap manufacturers have created small bars of soap, somewhat more than a single wash. These smaller bars of soap are often decorative, for example shaped like seashells. Such bars of soap are often avoided because they look like decoration and or the user does not want to discard the small bar after they are done washing their hands. Hotels have a similar situation, providing a small, wrapped bar of soap for each room. The bar is often large enough for one to use for a whole week, but often the customer only stays one night, creating waste.

Single servings of soap products are known in the industry, to some extent. None provide a single-use soap bar that adequately lathers a user's hands and/or face. For example, the small bars cited above have a minimum size dictated by the amount of soap that can be delivered during a reasonable amount of time while rubbing under warm water. If made too small, insufficient soap suds would result. As said before, if made too big, the residual soap bar would have to be saved or discarded.

Single serving soap packets are known in the dishwashing and laundry markets. Laundromats often sell packages of laundry soap, bleach, softener, etc. that are sized for a single wash. Dishwasher soap now comes in plastic pouches that dissolve from the heat of the dishwasher water. U.S. Pat. No. 3,186,869 to Friedman disclose a coated film laundry package that has a coating that dissolves when exposed to water in the washing machine. Additionally, U.S. Pat. No. 2,539,395 to Banks discloses a water disintegratable soap package. Such packets could be scaled down to the size of a single use hand soap package, but the packet would not dissolve quickly enough to meet the time expectations of a typical user. Furthermore, there would be a small amount of residual packaging that remains during the washing that would not feel right to the user.

U.S. Pat. No. 2,470,851 to Hermanson discloses a soap powder packet that contains powdered soap. The packet is made from a thin paper web, through which water can flow, thereby wetting the powdered soap and producing soap suds. This device has the same problem of the amount of time it takes to produce sufficient lather, but also has a disposal issue, being that the paper web outer layer must be discarded.

U.S. Pat. No. 4,718,556 to Hildebrandt discloses a bag that contains, for example, liquid soap. The packet is made from a thin sheet of material that can be easily torn, thereby dispensing the liquid. This device delivers soap in a reasonable time, but has a disposal issue, being that the outer layer must be discarded.

U.S. Pat. No. 1,993,174 to Coney discloses a wash cloth with a pouch for containing powdered or granular soap. This device has a similar problem with the amount of time it takes to produce sufficient lather, but has a disposal issue, being that the entire washcloth must be discarded after use.

It is evident from the many prior inventions that there exists a need for individual servings of hand soap. What is needed is an individual serving of hand soap that provides lather/suds quickly while substantially dissolving without the need to discard any waste.

SUMMARY OF THE INVENTION

In one embodiment, an individual liquid-filled soap is disclosed including a thin, breakable, solid soap outer shell and a liquid contained within the thin, solid soap outer shell.

In another embodiment, a method for washing hands is disclosed including providing an individual liquid-filled soap that has a thin, breakable, solid soap outer shell and a liquid contained there within. The individual liquid-filled soap is rubbed with water between a user's hands, thereby breaking the thin, solid soap outer shell and the user washes their hands using the individual liquid-filled soap and the liquid. When finished washing, any remnants of the individual liquid-filled soap is allowed to flush down the drain.

In another embodiment, an individual liquid-filled soap is disclosed including a liquid washing agent and a container for holding the liquid washing agent, the container being made from a thin, breakable layer of solid soap.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE INVENTION

Figure 1:
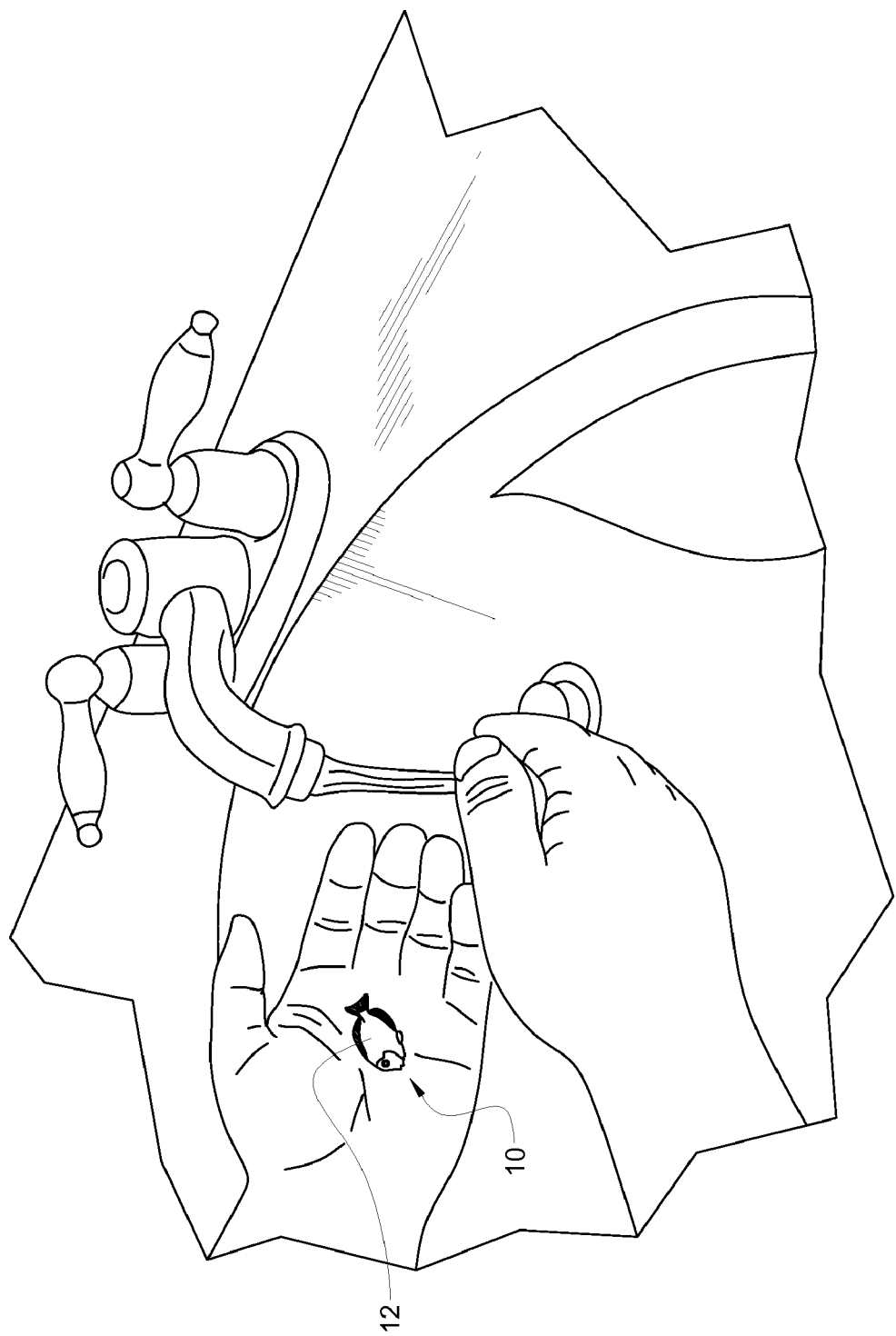
FIG. 1 illustrates a schematic view of an individual soap of the present invention in use.

Reference will now be made in detail to the presently preferred embodiments of the invention, examples of which are illustrated in the accompanying drawings. Throughout the following detailed description, the same reference numerals refer to the same elements in all figures.

Referring to FIG. 1, a schematic view of an individual soap of the present invention in use will be described. As will be shown, the individual soap 10 has a thin, breakable solid soap outer layer 12. The user places the individual soap 10 in their hands and under slight pressure, the individual soap 10 breaks, providing both solid soap and a liquid core to lather the user's hands. After the user finishes washing their hands, the outer layer 12 of solid soap is either completely consumed or in small granular pieces that easily wash down the drain. By using a thin layer of solid soap as the outer layer 12, the individual soap 10 can be formed into various decorative shapes such as a fish shape as shown, a round shape, a seashell, alphabet letters (e.g., the family's last name), hotel logos, etc.

Figure 2:
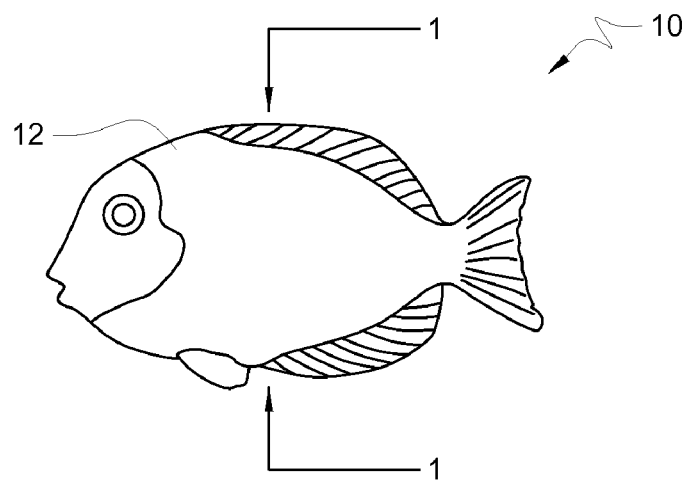
FIG. 2 illustrates a schematic view of an individual soap of the present invention in the form of a fish.

Referring to FIG. 2, a schematic view of an individual soap of the present invention in the form of a fish will be described. The individual soap 10 has a thin, breakable solid soap outer layer 12. In this embodiment, the thin, breakable solid outer layer 12 is made from solid soap, thereby lending the individual soap 10 to be formed or shaped into whatever shape is desired.

Figure 3:
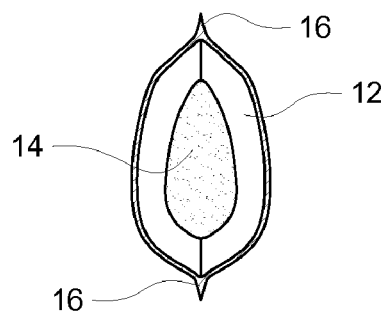
FIG. 3 illustrates a cross-section view along lines 1-1 of FIG. 1 of an individual soap of the present invention in the form of a fish.

Referring to FIG. 3, a cross-section view along lines 1-1 of FIG. 1 of an individual soap of the present invention in the form of a fish will be described. The thin, breakable solid outer layer 12 is thick enough to provide structure and shape to the individual soap 10 and thin enough to dissolve and/or break during washing of one's hands. In the preferred embodiment, the individual soap 10 is filled with a liquid washing agent or liquid 14. The liquid 14 is a soap compatible liquid such as liquid soap, lanolin, antibacterial lotion, antibacterial soap, hand lotion and the like. In some embodiments, the liquid washing agent 14 is liquid soap for quick lathering. In other embodiments, the liquid washing agent 14 is or includes other agents to improve the washing operation. For example, hand lotion or lanolin improves skin tone after washing while antibacterial agents kill germs.

The decorative fish shape has fins 16 made of the same solid soap as the thin solid outer layer 12.

Figure 4:
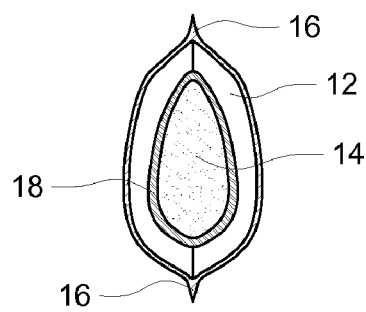
FIG. 4 illustrates a cross-section view along lines 1-1 of FIG. 1 of an individual soap of a second embodiment of the present invention in the form of a fish.

Referring to FIG. 4, a cross-section view along lines 1-1 of FIG. 1 of an individual soap of a second embodiment of the present invention in the form of a fish will be described. The thin solid outer layer 12 is thick enough to provide structure and shape to the individual soap 10 and thin enough to dissolve and/or break during washing of one's hands. In the preferred embodiment, the individual soap 10 is filled with a liquid 14. The liquid 14 is a soap compatible liquid such as liquid soap, lanolin, antibacterial lotion, antibacterial soap, hand lotion and the like. Some types of liquid 12 react with the thin solid outer layer 12, thereby softening or dissolving the thin solid outer layer 12. Therefore, in some embodiments, an intermediate layer 18 is provided. In some embodiments, this layer 18 is a petroleum-based coating such as oil or wax. In some embodiments, this layer 18 is an oil-based coating such as cooking oil or olive oil. In some embodiments, this layer 18 is a dissolvable film. The decorative fish shape has fins 16 made of the same solid soap as the thin solid outer layer 12.

Figure 5:
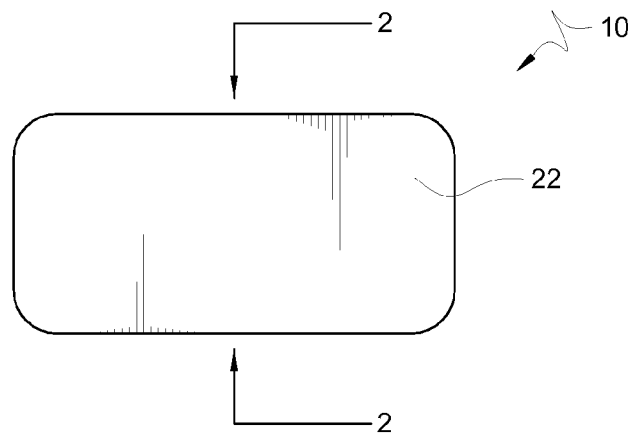
FIG. 5 illustrates a schematic view of an individual soap of the present invention in the form of a typical bar of soap.

Referring to FIG. 5, a schematic view of an individual soap of the present invention in the form of a typical bar of soap will be described. The individual soap 10 has a thin, breakable solid soap outer layer 12. In this embodiment, the thin, breakable solid outer layer 12 is made from solid soap, thereby lending the individual soap 10 to be formed or shaped into whatever shape is desired; as shown, a typical soap bar shape.

Figure 6:
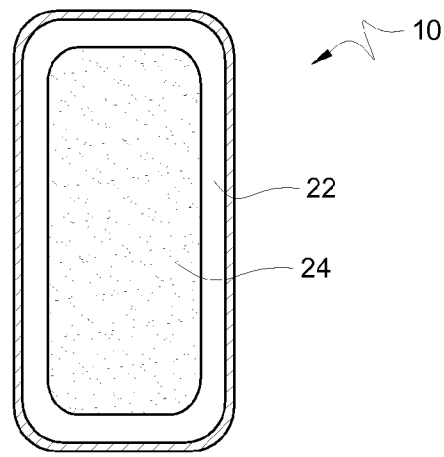
FIG. 6 illustrates a cross-section view along lines 2-2 of FIG. 5 of an individual soap of the present invention in the form of a typical bar of soap.

Referring to FIG. 6, a cross-section view along lines 2-2 of FIG. 5 of an individual soap of the present invention in the form of a typical bar of soap will be described. The thin, breakable solid outer layer 22 is thick enough to provide structure and shape to the individual soap 10 and thin enough to dissolve and/or break during washing of one's hands. In the preferred embodiment, the individual soap 10 is filled with a liquid 24. The liquid 24 is a soap compatible liquid such as liquid soap, lanolin, antibacterial lotion, antibacterial soap, hand lotion and the like.

Figure 7:
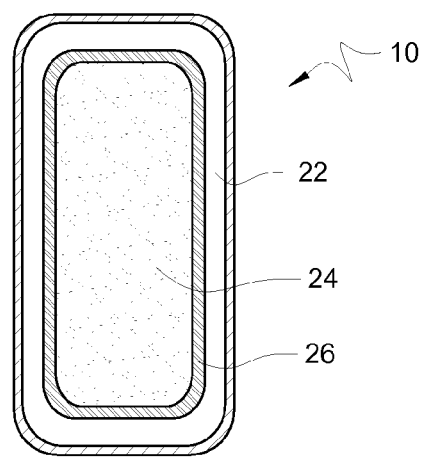
FIG. 7 illustrates a cross-section view along lines 2-2 of FIG. 5 of an individual soap of a second embodiment of the present invention in the form of a typical bar of soap.

Referring to FIG. 7, a cross-section view along lines 2-2 of FIG. 5 of an individual soap of a second embodiment of the present invention in the form of a typical bar of soap will be described. The thin, breakable solid outer layer 22 is thick enough to provide structure and shape to the individual soap 10 and thin enough to dissolve and/or break during washing of one's hands. In the preferred embodiment, the individual soap 10 is filled with a liquid 24. The liquid 24 is a soap compatible liquid such as liquid soap, lanolin, antibacterial lotion, antibacterial soap, hand lotion and the like. Some types of liquid 24 react with the thin solid outer layer 22, thereby softening or dissolving the thin solid outer layer 22. Therefore, in some embodiments, an intermediate layer 26 is provided. In some embodiments, this layer 26 is a petroleum-based coating such as oil or wax. In some embodiments, this layer 26 is an oil-based coating such as cooking oil or olive oil. In some embodiments, this layer 26 is a dissolvable film.

The individual soap 10 of the present invention lends itself to be individually packaged or bulk packaged. One or more individual soaps 10 are dispensed in a soap dish near a wash basin within reach of a person wishing to wash their hands.

Equivalent elements can be substituted for the ones set forth above such that they perform in substantially the same manner in substantially the same way for achieving substantially the same result.

It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. An individual liquid-filled soap comprising:
   a thin, breakable, solid soap outer shell;
   a liquid contained within the thin, solid soap outer shell; and
   an intermediate layer, the intermediate layer disposed between the thin, breakable, solid soap outer shell and the liquid, the intermediate layer insulates the thin, breakable, solid soap outer shell from the liquid;
   whereas the intermediate layer is made of a material selected from the group consisting of a petroleum-based coating, oil, wax, an oil-based coating, cooking oil, olive oil and a dissolvable film;
   whereas the liquid remains in a liquid state.

2. The individual liquid-filled soap of claim 1, wherein the liquid is selected from one or more of the group of liquids comprising liquid soap, lanolin, hand cream, antibacterial soap, and antibacterial cream.

3. The individual liquid-filled soap of claim 1, wherein the thin, breakable, solid soap outer shell is fish-shaped.

4. The individual liquid-filled soap of claim 1, wherein the intermediate layer comprises a petroleum-based material.

5. The individual liquid-filled soap of claim 1, wherein the intermediate layer comprises wax.

6. The individual liquid-filled soap of claim 1, wherein the intermediate layer comprises a cooking-oil based material.

7. A method for washing hands, the method comprising:
   providing an individual liquid-filled soap comprising:
      a thin, breakable, solid soap outer shell;
      a liquid contained within the thin, breakable, solid soap outer shell; and
      an intermediate layer, the intermediate layer disposed between the thin, breakable, solid soap outer shell and the liquid, the intermediate layer insulates the thin, breakable, solid soap outer shell from the liquid;

whereas the intermediate layer is made of a material selected from the group consisting of a petroleum-based coating, oil, wax, an oil-based coating, cooking oil, olive oil and a dissolvable film;

whereas the liquid remains in a liquid state;

rubbing the individual liquid-filled soap with water between a user's hands, thereby breaking the thin, breakable, solid soap outer shell;

washing the user's hands using the thin, breakable, solid soap outer shell and the liquid; and allowing any remnants of the individual liquid-filled soap to flush down a drain.

8. The method for washing hands of claim 7, wherein the liquid is selected from one of more of the group of liquids comprising liquid soap, lanolin, hand cream, antibacterial soap, and antibacterial cream.

9. The method for washing hands of claim 7, wherein the thin, breakable, solid soap outer shell is fish-shaped.

10. The method for washing hands of claim 7, further comprising an intermediate layer adapted to insulate the thin, breakable, solid soap outer shell from the liquid.

11. The method for washing hands of claim 10, wherein the intermediate layer comprises a petroleum-based material.

12. The method for washing hands of claim 10, wherein the intermediate layer comprises wax.

13. The method for washing hands of claim 10, wherein the intermediate layer comprises a cooking-oil based material.

14. An individual liquid-filled soap comprising:

a liquid washing agent;

a means for containing the liquid washing agent, the means for containing the liquid washing agent made from a thin, breakable layer of solid soap; and a means for insulating the means for containing the liquid washing agent from the liquid washing agent, the means for insulating disposed between the means for containing and the liquid washing agent, the means for containing made from a material selected from the group consisting of a petroleum-based coating, oil, wax, an oil-based coating, cooking oil, olive oil and a dissolvable film;

whereas the liquid remains in a liquid state.

15. The individual liquid-filled soap of claim 14, wherein liquid washing agent is selected from the group of liquids comprising liquid soap, lanolin, hand cream, antibacterial soap, and antibacterial cream.

16. The individual liquid-filled soap of claim 14, wherein the means for insulating comprises a petroleum-based material.

17. The individual liquid-filled soap of claim 14, wherein the means for insulating comprises wax.

18. The individual liquid-filled soap of claim 14, wherein the means for insulating comprises a cooking-oil based material.

\* \* \* \* \*